(12) United States Patent
Gendre et al.

(10) Patent No.: US 6,472,149 B1
(45) Date of Patent: Oct. 29, 2002

(54) METHOD FOR DETECTING LIVE MICROBIOLOGICAL CONTAMINANTS IN A FOOD PRODUCT SAMPLE

(75) Inventors: François Gendre, Strasbourg (FR); Pierre Brignon, Strasbourg (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 09/297,136

(22) PCT Filed: Oct. 27, 1997

(86) PCT No.: PCT/FR97/01918

§ 371 (c)(1),
(2), (4) Date: Apr. 26, 1999

(87) PCT Pub. No.: WO98/18958

PCT Pub. Date: May 7, 1998

(30) Foreign Application Priority Data

Oct. 28, 1996 (FR) .............................................. 96 13125

(51) Int. Cl.⁷ ........................... C12Q 1/68; C12P 19/34; C07H 21/04
(52) U.S. Cl. ....................... 435/6; 435/91.2; 435/91.51; 536/24.3; 536/24.32
(58) Field of Search ......................... 435/91.2, 6, 91.51; 536/24.3, 24.32

(56) References Cited

U.S. PATENT DOCUMENTS 4,965,188 A * 10/1990 Mullis et al. .................. 435/6
5,004,682 A * 4/1991 Roberts et al. ................ 435/6

FOREIGN PATENT DOCUMENTS

| EP | 0 133 671 | 3/1985 | ............ C12Q/1/68 |
| WO | WO 90/11370 | 10/1990 | ............ C12Q/1/68 |
| WO | WO 92/03455 | 3/1992 | ............ C07H/15/12 |

OTHER PUBLICATIONS

Lunegerg et al., Detection of Mycoplasma pneumoniae by polymerase chain reaction and nonradioactive hybridization in microtiter plates, J. of Clinical. Micriobiology, 1993, vol. 31(5), pp. 1088–1094.*

Vliet et al. Assessment of mycobacterial viability by RAN amplification, Antimicrobial agents and chemotherapy, 1994, vol. 38(9), pp. 1959–1965.*

Silbaq et al. Nucleotide sequence of Mycobacterium Ieprae elongation factor (EF–Tu) gene, Nucleic Acid Research, vol. 21(14), p. 3327, 1993.*

Cottrelle et al. Cloning, nucleotide sequence, and expression of one of two genes coding for yeast elongation factor 1 alpha, The J. of Biological Chemistry, vol. 260 (5), pp. 3090–3096, 1985.*

S. Berg, et al., "Development of an Amplification and Hybridization Assay for the Specific and Sensitive Detection of Mycoplasma Fermentans DNA", Mol. & Cell. Probes, vol. 10, pp. 7–14 (1996).

Montorres et al., "RT–PCR and Gene Expression", The Polymerase Chain Reaction, 277–94 (1994); XP 002034388.

Derwent Publications Ltd., Database WPI, Section Ch, Week 9748, Class B04, AN 97–520740 (1997); XP002054735.

* cited by examiner

Primary Examiner—Gary Benzion
Assistant Examiner—Joyce Tung
(74) Attorney, Agent, or Firm—Finnegan, Henderson, Farabow, Garrett & Dunner, L.L.P.

(57) ABSTRACT

A process for detecting live microbiological contaminants in a food product sample, according to which the presence of mRNA coding for the synthesis of a protein involved in the synthesis of proteins by the contaminants is detected in the sample.

16 Claims, 3 Drawing Sheets

METHOD FOR DETECTING LIVE MICROBIOLOGICAL CONTAMINANTS IN A FOOD PRODUCT SAMPLE

FIELD OF THE INVENTION

The present invention relates to a process for detecting live microbiological contaminants in a food product sample.

DESCRIPTION OF THE RELATED ART

Food products are particularly susceptible to contamination with microbiological products, in particular with bacteria, on account of the powerful effect which a contamination has on the health of the persons ingesting the food. In this sphere, live, and therefore active, microorganisms are particularly formidable since they are then able to propagate in the body and transmit severe diseases. There is therefore a definite need to develop a process which enables these live microorganisms to be detected in food products in a manner which is both precise and satisfactory.

A large number of methods exist for detecting bacteria, in particular, in samples. One which may be mentioned, by way of example, is that of culturing the sample in order to increase the number of bacterial cells present until colonies, which can be counted, are observed. Where appropriate, the culture can be followed by an additional step which enables the particular type of bacteria contained in the sample to be identified. These bacteriological methods require a great deal of time and skill on the part of the individuals who carry them out. Thus, it is generally necessary, for example, to incubate for from 24 to 48 hours before being certain of obtaining a positive or negative result.

Other methods have also been envisaged for eliminating the drawbacks of the conventional bacteriological method. Thus, microscopy is frequently used for detecting bacteria in clinical samples. Usually, it is necessary to stain the sample in order to increase the detection limits, a procedure which on the one hand represents a laborious method and, on the other hand, is unsuitable for food samples (1). Some immunological methods have also been successfully developed for detecting certain species which possess surface antigens which can be recognized by specific antibodies. However, such an approach cannot be used for qualitatively determining bacteria in a sample which may contain a large variety of bacterial species which do not possess a common surface antigen.

The European Patent Application EP-A-0 133671 describes a method for determining the presence of bacteria in samples, in particular in media, such as body fluids, which are suitable for diagnostic purposes, which employs nucleic acid hybridization techniques. According to this method, the sample to be tested is first of all subjected to denaturing conditions so as to render the nucleic acids of the bacteria, which are present in the sample, single-stranded. The resulting single-stranded nucleic acids are brought into contact with a polynucleotide probe which possesses a sequence which is homologous with at least one sequence which is common to all the bacterial species which are present in the sample. The probe and the denatured nucleic acids are brought into contact so as to effect a hybridization between the probe and the respective sequences of the bacteria. More particularly, the probe employed comprises at least a part of one of the strands of a gene which codes for the synthesis of a nucleic acid or a protein which is involved in the mechanism by which the proteins are synthesized. Those genes of this type which are cited are, in particular, genes which encode transfer RNAs, ribosomal RNAs, or initiation, elongation or translation termination factors. One of the features of this method is that it is not based on expression but rather on the presence of hybridizable nucleic acids, for example the RNA or the genomic DNA or the extra-chromosomal nucleic acids of the bacteria which are present. The result, which the Applicant views as being an advantage, of this is that the samples do not have that it is not based on expression but rather on the presence of hybridizable nucleic acids, for example the RNA or the genomic DNA or the extra-chromosomal nucleic acids of the bacteria which are present. The result, which the Applicant views as being an advantage, of this is that the samples do not have to be treated so as to guarantee the viability of the bacteria which are present.

Document WO 92/03455 describes compositions and processes for treating and diagnosing infections with Candida, in particular nucleotides which are able to hybridize specifically with a part of the Candida MRNA, in particular the mRNA encoding elongation factors 1 and 2 (TEF1 and TEF2). This document is only directed towards therapeutic or diagnostic applications, either for detecting the presence of Candida in a patient or for inhibiting the activity of this bacterium by blocking the expression of essential proteins.

The document Berg et al., "MOL CELL. PROBES, Vol. 10, February 1996, pp 7–14" describes a system for specifically detecting the DNA of microplasmas using the PCR technique. Although it is indicated, on page 12 of this document, that the target sequence for the PCR amplification is the tuf gene, which encodes the elongation factor Tu, this document is only directed towards detecting DNA, and not mRNA on the one hand, and, on the other hand, the method is only a method for detecting bacteria in order to establish a diagnosis in a patient. This document does not envisage any application in the sphere of the invention, in which the specific problem is that of detecting living bacteria.

Thus, there is no known method which makes it possible to detect live microbiological contaminants in a food product and which at the same time discriminates between the live microorganisms and the dead microorganisms and which, moreover, does not pose any problems relating to public health.

SUMMARY OF THE INVENTION

The inventors have now discovered that it was possible to detect live microbiological contaminants in a food product sample by detecting, in this sample, the resence of messenger RNA (mRNA) which codes for the synthesis of a protein which is involved in the mechanism by which the proteins of the said contaminants are synthesized.

Different families of microorganisms can be detected in accordance with the invention. Procaryotes, in particular bacteria, unicellular eucaryotes, in particular yeasts, and multicellular eucaryotes, in particular fungi, may be mentioned in a nonlimiting manner. Different species can be identified within these families. Thus, for example, Escherichia, Salmonella and Mycobacterium in the case of bacteria; Saccharomyces and Candida in the case of yeasts; Mucor, Neurospora and Trichoderma in the case of fungi.

The synthesis of proteins by microorganisms comprises steps of transcription and translation. Within the context of translation, nucleic acids and proteins exist which are involved in each of the three basic steps of protein synthesis, i.e. initiation, elongation and termination. invention in order to detect live microbiological contaminants belonging to different species.

DETAILED DESCRIPTION OF THE INVENTION

Thus, according to one preferred embodiment, the invention relates to a process for non-specifically detecting live contaminants belonging to different species of a family of microorganisms, according to which the MRNA detected is an mRNA which codes for the synthesis of a protein whose primary structure is at least partially conserved between different species.

On the contrary, if a greater specificity of detection between different microorganism species is required, it is possible, according to the invention, to detect different mRNAs which respectively code for the synthesis of a protein whose primary structure is not conserved between different species.

Of all the factors which are involved in protein synthesis, one example which is particularly preferred consists of the elongation factors. Those of these factors which may be mentioned are the EF-1, EF-2, EF-G and EF-TU factors, in the case of bacteria (2), or else the EF-1α factor (3) in the case of yeasts and fungi. These factors play a fundamental role in protein synthesis in that they determine the length of time during which an aminoacyl tRNA remains associated with the ribosome and with the forming polypeptide chain, which function is referred to by the expression "kinetic proofreading" (4).

There are various reasons why it is particularly advantageous to look for the presence of messenger RNA which encodes an elongation factor. First of all, this gene represents a very suitable marker of the viability of the cells since inactivation of this gene is a lethal event both in procaryotes and eucaryotes (5, 6). Furthermore, the gene which encodes an elongation factor encodes a protein which belongs to those proteins which are most widely expressed in procaryotes and eucaryotes (7, 8), a fact which makes it possible to substantially decrease the cell detection level. Finally, as pointed out above, it is possible to modulate the specificity of the detection insofar as this function is conserved in procaryotes and eucaryotes and the primary structure of this type of gene is very similar (9). It is thus possible to implement means of detection which make it possible to distinguish between procaryotes and eucaryotes or, on the contrary, to non-specifically detect bacteria, yeasts and/or fungi at one and the same time.

Furthermore, mRNA encoding elongation factors has a very short half-life (10, 11). Its presence therefore reveals the presence of cells which were still alive approximately ten minutes before the mRNA was detected.

An mRNA encoding an elongation factor is therefore detected in accordance with a preferred embodiment. In this case, a live microorganism cell within the meaning of the invention is a cell which is able to produce the mRNA corresponding to an elongation factor.

The RT-PCR (polymerase chain reaction combined with reverse transcription) is a method of choice for detecting the presence of messenger RNA according to the invention. This technique consists in carrying out a PCR on an RNA which has previously been transcribed into complementary DNA in the presence of reverse transcriptase and a primer. After the RT stage, the proper PCR stage is carried out under standard conditions in the presence of the DNA to be amplified, two oligonucleotide primers which flank the region to be amplified and four deoxynucleotide triphosphates (DATP, dCTP, dGTP and dTTP), in large molar excess, and the enzyme Taq polymerase.

Naturally, the choice of the primers is a basic requirement, since it makes it possible to target the mRNA which it is desired to detect. The oligonucleotide primers are prepared such that they are specific for the coding region of a gene which encodes an elongation factor. The known elongation factors which are preferably selected are the EF-TU factor in the case of bacteria and the EF-1α factor in the case of yeasts and fungi. It is for this reason that the primers B1/B2 (5' CGCTGGAAGGCGACGMRRAG 3' (SEQ ID NO:1)/5' CGGAAGTAGAACTGCGGACGGTAG 3' (SEQ ID NO:2) were, for example, prepared, which primers are specific for a fragment of the bacterial EF-TU elongation factor which is found, in particular, in *Salmonella typhimurium, Mycobacterium tuberculosis, Mycobacterium leprae, Escherichia coli, Brevibacterium linens* and *Streptomyces ramocissimus*.

In the case of yeasts, the primers L1/L2 (5' TCCATGG-TACAAGGGTTGGGAA 3' (SEQ ID NO:3)/5' GCGAATC-TACCTAATGGTGGGT 3' (SEQ ID NO:4) were prepared, which primers are specific for a fragment of the yeast EF-1α elongation factor, which is found both in *Saccharomyces cerevisiae* and *Candida albicans*.

Finally, an example of a nucleotide primer which can be used for detecting messenger RNA which is specific for fungi consists of the pair M1/M2 (5' GCTGGTATCTC-CAAGGATGG 3' (SEQ ID NO:5)/5'-CGACGGACTTGACTTCRGTGG 3' (SEQ ID NO:6). These primers are more particularly specific for a fragment of the fungal EF-1α elongation factor which is found in *Mucor racemosus, Neurospora crassa, Trichoderma reesei, Absidia glauca, Aureobasidium pullulans, Histoplasma capsulatum* and *Puccinia graminis*.

The primers which can be used in accordance with the invention were prepared after comparing the elongation factor-encoding regions of different microorganism species (Lasergene software, Dnastar, Madison, Wis., USA).

In a general manner, the process according to the invention can be characterized by the following steps taken together:

a) a sample of the food product to be tested is withdrawn;

b) the cells are lysed;

c) reverse transcription is carried out;

d) amplification cycles are carried out using oligonucleotide primers which are specific for the coding region of a gene which encodes an elongation factor;

e) the amplification products are separated;

f) the amplification products are visualized.

g) the products as visualized in step f) are compared with the amplification products which are obtained from pure mRNA.

Since the invention is essentially directed towards detecting live microbiological contaminants, it is particularly advantageous to as far as possible remove any additional contamination of the medium with the DNA which is present in the sample. For this reason, according to a preferred embodiment of the invention, an additional step (b'), which is intended to remove the DNA which is present in the sample, is added after step b). For this, DNase I, which does not contain any RNase, can simply be added to the reaction medium. If it is desired to check for the absence of false positives which are linked to the presence of DNA, one possibility consists in carrying out a PCR reaction on the same samples as those used for the RT-PCR.

The invention will be illustrated in more detail by the embodiments which follow and which are accompanied by FIGS. 1 to 3.

Examples were carried out with the following strains:

*Escherichia coli* (strain ATCC 19110);

*Saccharomyces cerevisiae* S288C;

*Mucor racemosus* (strain CBS 11308).

While the sample on which the process was performed is milk, the invention can of course be applied to any other, preferably liquid, food product.

EXAMPLE 1

Determining the Presence of Live *E. coli* Cells in Milk (Detecting the mRNA Encoding the EF-Tu Elongation Factor)

a) Preparing the Strain

An *E. coli* strain is cultured at 37° C. in Luria broth, and then a solid medium is prepared by adding 2% agar (Difco Laboratories). A portion of the cells is removed during the exponential phase of growth. The cells are divided up into samples of 2 ml and then subjected to lethal conditions by incubating them at 65° C. for 15 min. Dilution series of the samples are plated out on agar medium in order to check the viability of the cells and to count them. Finally, the samples are used for inoculating samples of commercially available cow's milk which has been pasteurized at ultrahigh temperature.

b) Contaminating the Milk

Concentration series of from 105 to one cell per ml of milk are made up. The possible interference of the milk in the PCR reaction is ruled out by carrying out 4 cycles of washing with PBS medium, as indicated in the Cooray et al. document (12), the contents of which is hereby incorporated by reference. After washing, the final milk pellet is resuspended in a volume of PBS equal to that of the original volume of milk, and this suspension is then filtered through a 25 mm-diameter polycarbonate membrane which has been moistened with PBS medium (0.8 μm pore size, Millipore). The filter is transferred into a 15 ml Falcon™ tube (Becton Dickinson). 1 ml of PBS is added and the whole is mixed vigorously for 30 seconds, after which the supernatent is recovered. A further 0.5 ml of PBS is then added to the filter and the resulting suspensions are combined together and then centrifuged at 5000 g for 5 min.

40 units of RNase inhibitor (Boehringer) are added to prevent the RNA being degraded, and water, which has been adjusted with 0.05% diethyl pyrocarbonate in order to inactivate nucleases, is added to a final volume of 50 μl, in accordance with the method described in Roszak et al. (13), the content of which is hereby incorporated by reference.

The cells are then lysed by adding 50 mg of glass microbeads (0.5 mm, Biospec Products, Bartlesville, Okla.). The tubes are shaken twice, with a 10 second interval, at 5000 rpm for 20 seconds, and are left on ice between two mixings. After decantation, 10 μl of the lysate is transferred to a new tube.

c) Removing the Genomic DNA

EZ buffer (Perkin Elmer kit), as reaction buffer for the 1-times concentrated rTth enzyme, 2.5 mmol of Mn(OAc)2 and, finally, 10 units of RNase-free DNase (I) (Boehringer), in order to prevent subsequent amplification of contaminating genomic sequences (14), are added to give a final volume of 20 μl. After incubating at 37° C. for 10 min, the DNase is inactivated by raising the temperature to 95° C. for 5 min.

d) RT-PCR

The two steps of RT and of PCR are carried out consecutively in the same tube. For the RT step, the following are added in order to give a final volume of 50 μl: 15 μl of lysate digested with DNase I, 1×EZ buffer, 1.4 mM of Mn(OAc)2, 0.3 mm of deoxyribonucleoside triphosphate (Perkin Elmer), 0.4 μM of primers B1 and B2 (5' CGCTGGAAG-GCGACGMRRAG 3' (SEQ ID NO:1)/5' CGGAAGTA-GAACTGCGGACGGTAG 3' (SEQ ID NO:2)) (upper and lower strands) and 5 units of rTth DNA polymerase (Perkin Elmer). The mixture is incubated for 2.5 min at 95° C., 20 min at 60° C. and 1 min at 95° C. For the PCR step, 40 cycles are carried out directly, with each cycle consisting of 15 seconds at 95° C. and 30 seconds at 60° C. A final extension is carried out for 10 min at 60° C.

e) Detecting False Positives

Checking to determine whether there are any false positives due to contamination with DNA is carried out by adding 5 μl of the DNase I-digested lysate, 1×Taq buffer (Boehringer), 0.05 mM of deoxyribonucleoside triphosphate, 0.4 μM of each of the primers B1 and B2, and 2.5U of Taq polymerase (Boehringer) to give a final volume of 50 μl.

f) Separating the Amplification Products

10 μl of the amplification products are separated by horizontal gel electrophoresis (1 to 2% agarose in EDTA tris-acetate), and the bands are visualized by staining with ethidium bromide and illuminating with UV light. Total RNA is also analyzed as a positive RT-PCR control (it is extracted using the RNAgent™ kit (Promega)), and the resulting amplification products are compared with those obtained from the total RNA. An optional step can be added in order to confirm the identity of the amplified products. For this, the bands of expected size are purified on a gel ("Gel Extract Kit", Qiagen) (462 bp fragment), and 1 μl of the DNA solution is then used as the template for a second PCR employing internal primers.

Figure 1:
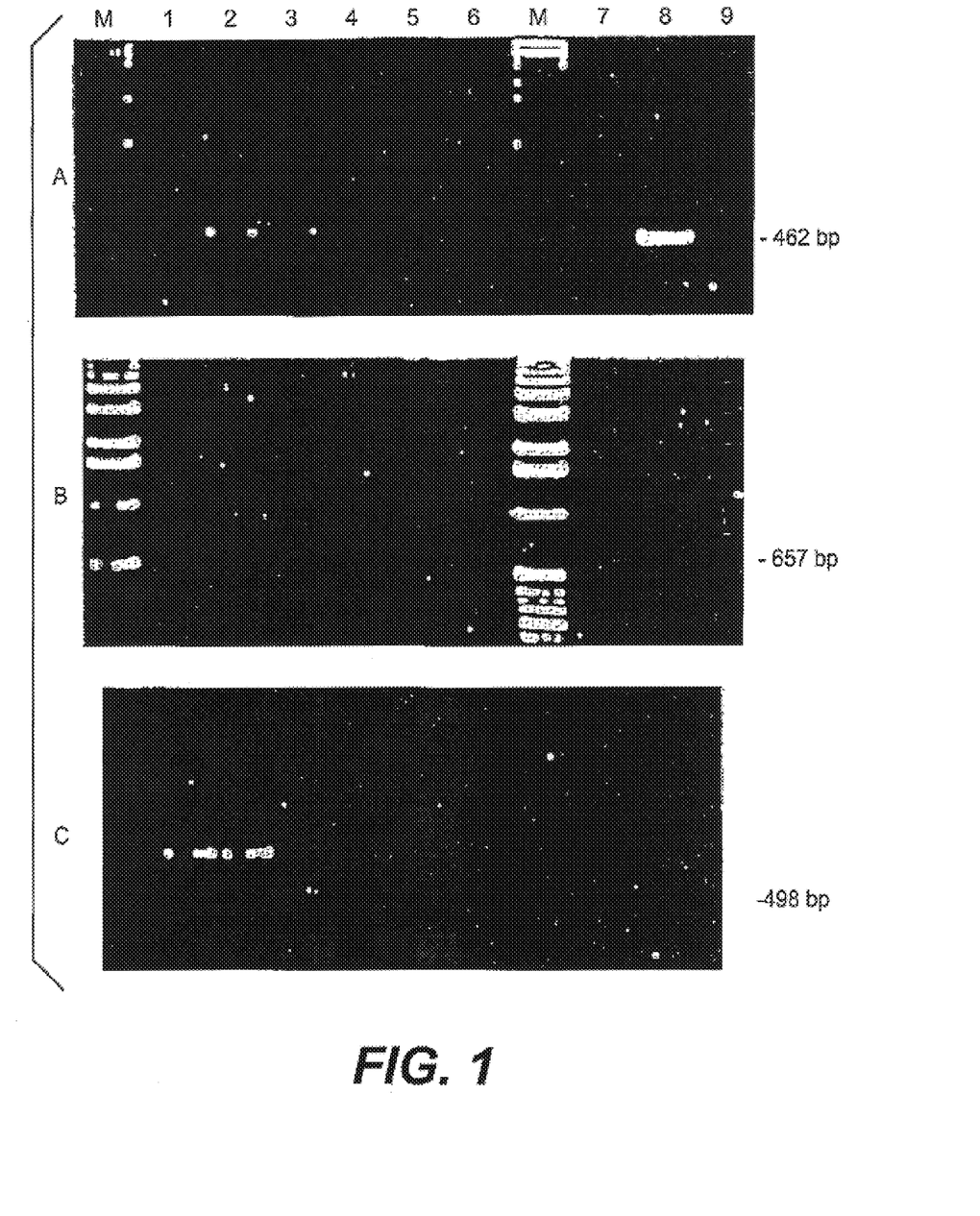
FIG. 1 depicts an electrophoresis gel of the RT-PCR products of the EF-Tu gene from *E. coli* (tuf b gene) (A) or of the EF-1α gene from S. cerevisiae (B) or from *M. racemosus* (C), suspended in milk in concentrations of from 105 cells/ml (lane 1) to 1 cell/ml (lane 6), while decreasing the concentration 10 times on each occasion. Lane 7 depicts a negative control without cells; lane 8 depicts a positive control with pure mRNA; lane 9 depicts a PCR which was carried out on a lysate which was digested with DNase I; the M lanes depict a 1 kb ladder (Gibco BRLTM).

Results It was possible to detect the elongation factor using 10 cells/ml, which corresponds to 5–10 cells per reaction tube in accordance with the procedure employed (FIG. 1A, lane 5). No transcript is detected below this level or in uncontaminated milk (FIG. 1A, lanes 6 and 7, respectively). No detectable PCR product appeared when using the cell lysate following treatment with the DNase I (FIG. 1A, lane 9). It therefore appears that adding a step of treatment with DNase I does indeed prevent contaminating genomic sequences from being amplified.

EXAMPLE 2

Figure 2:
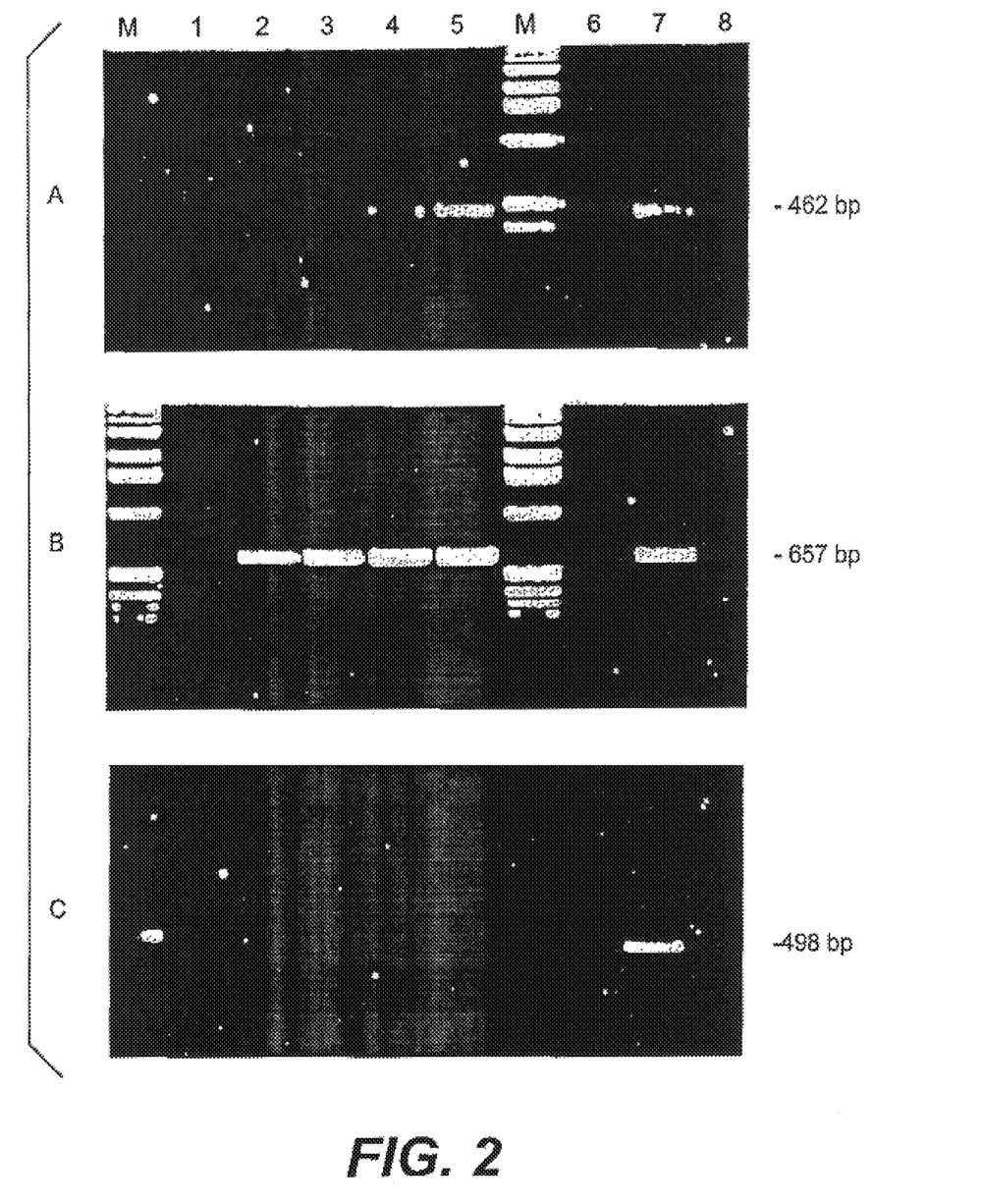
FIG. 2 depicts an electrophoresis gel of the RT-PCR products of the EF-Tu gene from *E. coli* (tuf b gene) (A) or of the EF-1α gene from *S. cerevisiae* (B) or from *M. racemosus* (C), suspended in milk at a cell concentration of 104–105 cells/ml. Lane 1 corresponds to 100% dead cells; lane 2 to 25% live cells and 75% dead cells; lane 3 to 50% dead cells and 50% live cells; lane 4 to 75% live cells and 25% dead cells; lane 5 to 100% live cells; lane 6 to a negative control without cells; lane 7 to a positive control with pure mRNA; lane 8 to a PCR carried out on a lysate digested with DNase (I); and lanes M to a 1 kb ladder (Gibco BRLTM).

Carrying Out an RT-PCR on a Milk Sample which is Contaminated Both with Living and Dead *E. coli* Cells When all the cells are dead (this was checked by plating out), the RT-PCR detection is negative (FIG. 2A, lane 1), which confirms that the RT-PCR method makes it possible to only detect living cells. Although producing quantitative results is difficult using conventional RT-PCR, gel electrophoresis analysis demonstrated a quantitative increase in the intensity of the specific bands when the number of viable cells increases (FIG. 2A, lanes 2 to 5), indicating an apparent increase in the target DNA of the RT-PCR procedure as the number of viable cells increases.

EXAMPLE 3

Determining the Presence of Living *S. cerevisiae* Cells in Milk (Detecting the MRNA Encoding the EF-1α Eelongation Factor)

The procedure of Example 1 is repeated apart from the following differences:

An *S. cerevisiae* S 288C strain is cultured at 30° C. in a YPD ("yeast peptone dextrose") medium containing 2% bactopeptone, 1% yeast extract (Difco Laboratories) and 2% glucose. A solid medium is then prepared by adding 2% agar (Difco Laboratories). A portion of the cells is withdrawn during the exponential phase of growth. The cells are divided up into samples of 2 ml and then exposed to lethal conditions by being incubated at 65° C. for 15 min.

When the RT-PCR is carried out, the following EF-1α elongation factor-specific olgionucleotide primers are employed:

L1 : 5' TCCATGGTACAAGGGTTGGGAA 3' (SEQ ID NO:3)

L2 : 5' GCGAATCTACCTAATGGTGGGT 3' (SEQ ID NO:4)

The same type of result is obtained as in Example 1 (FIG. 1B, detecting a fragment of 657 bp in size).

EXAMPLE 4

Carrying Out the RT-PCR on a Milk Sample which is Contaminated with Both Living and Dead *S. cerevisiae* Cells The same type of results is observed as in Example 2 (FIG. 2B).

EXAMPLE 5

Determining the Presence of Living *M. racemosus* Cells in Milk (Detecting the mRNA Encoding the EF-1α Elongation Factor)

The procedure of Example 1 is repeated except that, in step a), the *M. racemosus* strain is cultured at 30° C. in a YPD medium containing 2% bactopeptone, 1% yeast extract (Difco Laboratories) and 2% glucose. A solid medium is then prepared by adding 2% agar (Difco Laboratories). A portion of the cells is withdrawn during the exponential phase of growth. The cells are divided up into samples of 2 ml and then exposed to lethal conditions by incubating them at 120° C. for 30 min.

Serial dilutions of the samples are plated out on OGY agar medium (MERCK) in order to check the viability of the cells and to count them.

When the RT-PCR is being carried out, the following EF-1α elongation factor-specific nucleotide primers are employed:

M1 : 5' GCTGGTATCTCCAAGGATGG 3' (SEQ ID NO:5)

M2 : 5' -CGACGGACTTGACTTCRGTGG 3' (SEQ ID NO:6)

The same type of result is obtained as in Example 1 (FIG. 1C, determining a fragment of 498 bp in size).

EXAMPLE 6

Carrying Out the RT-PCR on a Sample of Milk which is Contaminated with Both Living and Dead *M. racemosus* Cells The same type of result is observed as in Example 2 (FIG. 2C).

EXAMPLE 7

Figure 3:
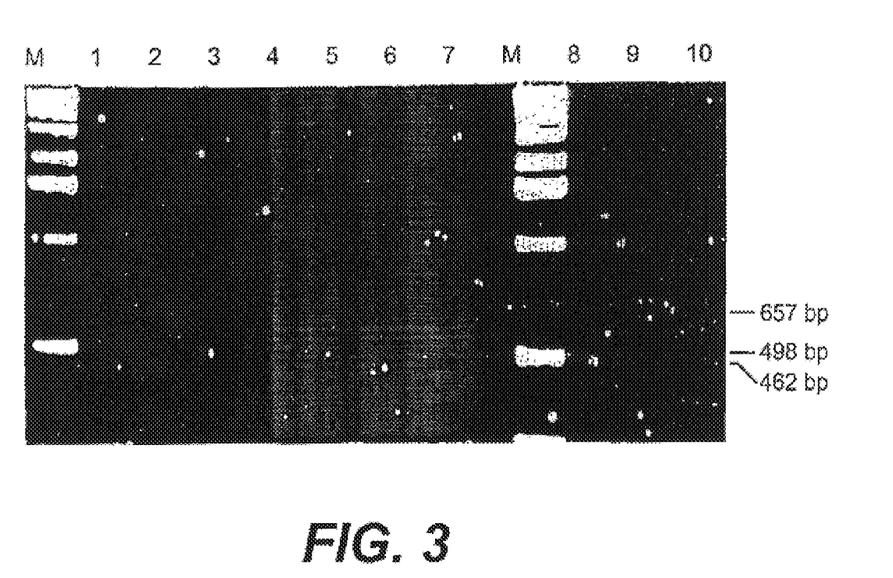
FIG. 3 depicts an electrophoresis gel of the RT-PCR products of the EF-Tu gene from *E. coli* (tuf b gene) and of the EF-la gene from *S. cerevisiae* and *M. racemosus*. The gel is obtained in one single RT-PCR step. The cells were suspended in milk at a concentration of 10 cells/ml. Lane 1, bacterial primers; lane 2, yeast primers; lane 3, fungal primers; lane 4, bacterial and yeast primers; lane 5, yeast and fungal primers; lane 6, bacterial and fungal primers; lane 7, bacterial, yeast and fungal primers; lane 8, negative control without cells; lane 9, positive control with pure mRNA; lane 10, PCR carried out on a lysate digested with DNase (I); M lanes, 1 kb ladder (Gibco BRLTM).

Determining the Simultaneous Presence of Living *E. coli, S. cerevisiae* and *M. racemosus* Cells The EF-Tu gene of *E. coli* and the EF-1α genes of *S. cerevisiae* and *M. racemosus* were detected simultaneously in one single reaction. The amplification products of expected size (fragments of 462 bp (*E. coli*) 675 bp (*S. cerevisiae*) and 498 bp (*M. racemosus*) in size, respectively) were detected simultaneously by means of RT-PCR using milk which was contaminated at one and same time with *E. coli, S. cerevisiae* and *M. racemosus*. For this, two (FIG. 3, lanes 4, 5 and 6) or three (FIG. 3, lane 7) pairs of primers were added to the same reaction mixture without modifying the RT-PCR conditions.

Thus, it appears that RT-PCR is a particularly powerful method for detecting viable contaminants on account of its great ability to increase detection sensitivities and the speed at which it can be carried out. It was possible to achieve a level of detection of 10 cells/ml of milk, and the whole of the RT-PCR process, including washing and filtering the milk sample, was performed in 4 hours without there being a need for a preliminary enrichment step. The choice of the target gene is important. It has thus been found to be particularly advantageous to select primers which are specific for the coding region of the elongation factor gene.

REFERENCES

1. BLACKBURN, C. de W. 1993. A review: rapid and alternative methods for the detection of salmonellas in food. J. Appl. Bacteriol. 75:199–214.
2. WEIJLAND, A., K. HARMARK, R. H. COOL, P. H. ANBAGH and A. PARMEGGIANI. 1992. Elongation factor Tu: a molecular switch in protein synthesis. Mol. Microbiol. 10 6:683–688.
3. MERRICK, W. C. 1992. Mechanism and regulation of eucaryotic protein synthesis. Microbiol. Rev. 56:291–315.

4. THOMPSON, R. C. 1988. EF-Tu provides an internal kinetic standard for translational accuracy. Trends Biochem. Sci. 13:91–93.
5. BOSH, L., B. KRAAL, P. H. VAN DER MEIDE, F. J. DUISTERVINKEL and J. M. VAN NOORT. 1983. The elongation factor EF-Tu and its two encoding genes. Prog. Nucleic Acid Res. Mol. Biol. 30:91–126.
6. COTREELE, P., M. COOL, P. THURIAUX, V. L. PRICE, D. THIELE, J. M. BUHLER and P. FROMAGEOT. 1985. Either one of the two yeast EF-1α genes is required for cell viability. Current Genetics. 9:693–697.
7. GORDON, J. 1970. Regulation of the in vivo synthesis of the polypeptide chain elongation factors in *Escherichia coli*. Biochemistry 9:912–917.
8. SCHIRMAIER, F. and P. PHILIPPSEN. 1984. Identification of two genes coding for the translation elongation factor EF-1α of *S. cerevisiae*. EMBO J. 3:3311–3315.
9. LUDWIG, W., M. WEIZENEGGER, D. BETZL, E. LEIDL, T. LENZ, A. LUDVIGSEN, D. MOLLENHOFF, P. WENZIG and K. H. SCHLEIFER. 1990. Complete nucleotide sequences of seven eubacterial genes coding for the elongation factor Tu: functional, structural and phylogenetic evaluations. Arch. Microbiol. 153:241–247.
10. CATTANEO, R. 1991. Different types of messenger RNA editing. Annu. Rev. Genet. 25:71–88.
11. NEIDHARDT, F. C., J. L. INGRAHAM and M. SCHAECHTER. 1990. Physiology of bacterial cell: a molecular approach Sinauer Associates Inc., Sunderland, Mass.
12. COORAY, K. J., T. NISHIBORI, H. XIONG, T. MATSUYAMA, M. FUJITA and M. MITSUYAMA. 1994. Detection of multiple virulence-associated genes of Listeria monocytogenes by PCR in artificially contaminated milk samples. Appl. Environ. Microbiol. 60:3023–3026.
13. ROSZACK, D. B. and R. R. COLWELL. 1987. Survival strategies of bacteria in natural environment. Microbiol. Rev. 51:365–379.
14. TONG, J., S. BENDAHHAR, H. CHEN and W. S. AGNEW. 1994. A simplified method for single RT-PCR that can detect and distinguish genomic DNA and mRNA transcripts. Nucl. Acid. Res. 22:3253–3254.

What is claimed is:

1. Process for distinguishing live microbiological contaminants from dead microbiological contaminants and detecting live microbiological contaminants in a food product sample, comprising detecting, in the sample, the presence of mRNA coding for a protein involved in the synthesis of proteins by the live contaminants, wherein the presence of mRNA is indicative of a presence of live microbiological contaminants in the sample.

2. Process according to claim 1 for nonspecifically detecting live contaminants belonging to different species of a family of microorganisms, wherein the mRNA codes for the synthesis of a protein whose primary structure is at least partially conserved between the different species.

3. Process according to claim 1, for specifically detecting live contaminants belonging to different species of a family of microorganisms, wherein the presence is detected of different mRNAs, each of which codes for a protein whose primary structure is not conserved between the different species.

4. Process according to claim 1, wherein the mRNA encodes an elongation factor.

5. Process according to claim 1, wherein the presence of mRNA is detected by performing a RT-PCR technique.

6. Process according to claim 5, wherein the oligonucleotide primers employed in the PCR are specific for the coding region of a gene which encodes an elongation factor.

7. Process according to claim 6 for detecting bacteria, wherein the elongation factor is the EF-Tu factor.

8. Process according to claim 6 for detecting yeasts or fungi, wherein the elongation factor is the factor EF-1α.

9. Process according to claim 1, wherein:
a) a sample of the food product to be tested is withdrawn;
b) the cells are lysed;
c) a reverse transcription is carried out;
d) amplification cycles are carried out using oligonucleotide primers
which are specific for the coding region of a gene which encodes an elongation factor;
e) the amplification products are separated;
f) the amplification products are visualized; and
g) the products as visualized in step f) are compared with the amplification products which are obtained from mRNA of known microorganism.

10. Process according to claim 9, further comprising a step b), which is directed toward removing the DNA which is present in the sample, is added after step b).

11. Process according to claim 9, further comprising a step which is directed toward verifying the absence of false positives linked to the presence of DNA.

12. Process for detecting live bacterial contaminants in a food product sample comprising cells that contain mRNA coding for an elongation factor, wherein the process comprises:
(a) providing a sample of the food product to be tested;
(b) reverse transcribing mRNA in said sample to produce cDNA;
(c) amplifying said cDNA by polymerase chain reaction (PCR); and
(d) detecting a coding region of a gene encoding elongation factor EF-Tu using a pair of oligonucleotide primers in the PCR that are specific for said coding region, wherein said pair of oligonucleotide primers is:
B1: 5' CGTGGAAGGCGACGMRRAG 3' (SEQ. ID NO. 1)
B2: 5' CGGAAGTAGAACTGCGGACGGTAG 3' (SEQ. ID NO. 2).

13. Process for detecting live yeast contaminants in a food product sample comprising cells that contain mRNA coding for an elongation factor, wherein the process comprises:
(a) providing a sample of the food product to be tested;
(b) reverse transcribing mRNA in said sample to produce cDNA;
(c) amplifying said cDNA by polymerase chain reaction (PCR); and
(d) detecting a coding region of a gene encoding elongation factor EF-1a using a pair of oligonucleotide primers in the PCR that are specific for said coding region, wherein said pair of oligonucleotide primers is:
L1: 5' TCCATGGTACAAGGGTTGGGAA 3' (SEQ. ID NO. 3)
L2: 5' GCGAATCTACCTAATGGTGGGT 3' (SEQ. ID NO. 4).

14. Process for detecting live fungal contaminants in a food product sample comprising cells that contain mRNA coding for an elongation factor, wherein the process comprises:

(a) providing a sample of the food product to be tested;

(b) reverse transcribing mRNA in said sample to produce cDNA;

(c) amplifying said cDNA by polymerase chain reaction (PCR); and (d) detecting a coding region of a gene using a pair of oligonucleotide primers in the PCR that are specific for said coding region, wherein said pair of oligonucleotide primers is:
M1: 5' GCTGGTATCTCCAAGGATGG 3' (SEQ. ID NO. 5)
M2: 5'-CGACGGACTTGACTTCRGTGG 3' (SEQ. ID NO. 6).

15. Process for detecting live microbiological contaminants in a food product sample comprising cells that contain mRNA coding for an elongation factor, wherein the process comprises:

(a) providing a sample of the food product to be tested, wherein the food product contains cells;

(b) lysing said cells;

(c) reverse transcribing mRNA;

(d) amplifying the product of step (c) using oligonucleotide primers specific for a coding region of a gene that encodes an elongation factor of a bacteria, yeast, or fungi;

(e) separating amplified products;

(f) detecting said amplified products; and (g) comparing products detected in step (f) with mRNA of a known microorganism;

wherein said oligonucleotide primers are selected from the group consisting of:

(1) B1: 5' CGCTGGAAGGCGACGMRRAG 3' (SEQ. ID NO. 1) and
B2: 5' CGGAAGTAGAACTGCGGACGGTAG 3' (SEQ. ID NO. 2)

(2) L1: 5' TCCATGGTACAAGGGTTGGGAA 3' (SEQ. ID NO. 3)
L2: 5' GCGAATCTACCTAATGGTGGGT 3' (SEQ. ID NO. 4), (3) M1: 5' GCTGGTATCTCCAAGGATGG 3' (SEQ. ID NO. 5), and
M2: 5'-CGACGGACTTGACTTCRGTGG 3' (SEQ. ID NO. 6).

16. Process for distinguishing live microbiological contaminants from dead microbiological contaminants and detecting live microbiological contaminants in a food product sample, according to which the presence of mRNA coding for the synthesis of a protein involved in the synthesis of proteins by the live contaminants is detected in the sample by performing RT-PCR technique, wherein said oligonucleotide primers comprise at least two of the primer pairs B1/B2, L1/L2, and M1/M2.

* * * * *

UNITED STATES PATENT AND TRADEMARK OFFICE
CERTIFICATE OF CORRECTION

PATENT NO.    : 6,472,149 B1
DATED         : October 29, 2002
INVENTOR(S)   : Francois Gendre and Pierre Brignon It is certified that error appears in the above-identified patent and that said Letters Patent is hereby corrected as shown below:

Column 11,
Line 60, after "primers" delete the line break.

Column 12,
Line 26, "step b)," should read -- step b'), --.
Line 44, "CGTGGAAGGCGACGMRRAG" should read
-- CGCTGGAAGGCGACGMRRAG --.

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,472,149 B1
DATED : October 29, 2002
INVENTOR(S) : François Gendre and Pierre Brignon

It is certified that error appears in the above-identified patent and that said Letters Patent is hereby corrected as shown below:

<u>Column 2,</u>
Line 65, after "termination." add the following:

-- It is thus possible to mention, as elements involved in this stage of translation, transfer, RNAs, ribosomal RNAs, ribosomal proteins, and initiation, elongation and termination factors. In fact, proteins or nucleic acids exist whose primary structure is at least partially conserved between different microorganism species belonging to one and the same family, and this property is advantageously exploited in accordance with the --

Signed and Sealed this

Twentieth Day of May, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
cgctggaagg cgacgmrrag                                               20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
cggaagtaga actgcggacg gtag                                          24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
tccatggtac aagggttggg aa                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4
gcgaatctac ctaatggtgg gt                                            22

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
gctggtatct ccaaggatgg                                              20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
cgacggactt gacttcrgtg g                                            21
```